United States Patent [19]

Ferrari

[11] Patent Number: 5,736,565

[45] Date of Patent: Apr. 7, 1998

[54] THERAPEUTIC COMPOUNDS SUITABLE FOR THE TREATMENT OF DISEASES CONNECTED WITH GLUTATHIONE DEFICIENCY, PROCESS FOR THEIR PREPARATION, AND PHARMACEUTICAL COMPOSITIONS CONTAINING SAME

[75] Inventor: Lorenzo Ferrari, Montecarlo, Monaco

[73] Assignee: Prospa B.V., Netherlands

[21] Appl. No.: 449,802

[22] PCT Filed: May 24, 1995

[86] PCT No.: PCT/EP93/03354

§ 371 Date: May 24, 1995

§ 102(e) Date: May 24, 1995

[87] PCT Pub. No.: WO94/12527

PCT Pub. Date: Jun. 9, 1994

[30] Foreign Application Priority Data

Nov. 30, 1992 [IT] Italy ................... MI92A2742

[51] Int. Cl.[6] ........................ A61K 31/40; C01D 201/12
[52] U.S. Cl. ........................... 514/423; 548/537
[58] Field of Search .................... 548/537; 514/423

[56] References Cited

U.S. PATENT DOCUMENTS 5,254,579 10/1993 Poli et al. ................. 548/551 X

FOREIGN PATENT DOCUMENTS

| 0332946 | 9/1989 | European Pat. Off. . |
| 0498268 | 12/1992 | European Pat. Off. . |
| 0515995 | 12/1992 | European Pat. Off. . |
| 3510858 | 10/1985 | Germany . |
| 1244010 | 6/1994 | Italy . |
| 2156818 | 10/1985 | United Kingdom . |

OTHER PUBLICATIONS

H. Sprince, C.M. Parker, G.S. Smith, and L.J. Gonzales, "Protection Against Acetaldehyde Toxicity in the Rat by L–Cysteine, Thiamin and L–2–Methylthiazolidine–4–carboxylic acid, Agents and Actions, vol. 4/2 (1974) pp. 125–130".

M. Frankel, D. Gertner, H. Jacobson, and L. Zilkha, "Syntheses of poly–S.alkyl–L–cysteines", J. Chem. Soc., 1960, 1390–1393.

R.J Aitken, J.S. Clarkson, and S. Fishel,"Generation of Reactive Oxygen Species, Lipid peroxidation, and Human Sperm Function", Biology of Reproduction, 40, 183–197 (1989).

G. Bellomo, F. Mirabelli, D. DiMonte, P. Richelmi, H. Thor, C. Orrenius and S. Orrenius,"Formation and Reduction of Gluthathione–protein Mixed Disulfides During Oxidative Stress", Bioch. Phar. vol. 36, No. 8, 1313–1320 (1987).

J. March, "Advanced Organic Chemistry", John Wiley & Sons, 3rd ed., 1985, pp. 371–374 and 348–351.

Biochemical Preparations, vol. 2, pp. 87–91, Erich G. Ball, John Wiley & Sons, Inc., (1952).

D. DiMonte, G. Bellomo, H. Thor, P. Nicotera and S. Orrenius, "Menadione–Induced Cytotoxicity is Associated with Protein Thiol Oxidation and Alteration in Intracellular $Ca^{+2}$ Homeostasis", Archives of Bioch. and Biophy., vol. 235, No. 2, Dec., pp. 343–350 (1984).

C.A.; 91:21136t; (1979), vol. 91, Inoue, et al.

*Primary Examiner*—Johann Richter
*Assistant Examiner*—Laura R. Gross
*Attorney, Agent, or Firm*—Hedman, Gibson & Costigan, P.C.

[57] ABSTRACT

The present invention is referred to sulphur-acylated derivatives of L-pyroglutamyl-L-cysteine of formula (I)

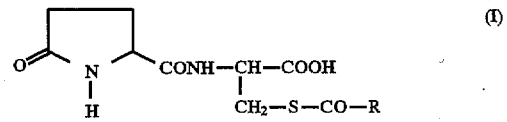

where R is a linear or branched alkyl containing 1 to 6 carbon atoms, their pharmaceutically acceptable salts, the process for their preparation, and the pharmaceutical compositions containing same. Said derivatives are suitable for the treatment of diseases connected with glutathione deficiency.

37 Claims, No Drawings

THERAPEUTIC COMPOUNDS SUITABLE FOR THE TREATMENT OF DISEASES CONNECTED WITH GLUTATHIONE DEFICIENCY, PROCESS FOR THEIR PREPARATION, AND PHARMACEUTICAL COMPOSITIONS CONTAINING SAME

This application is a 371 of PCT/EP93/03354 filed Nov. 30, 1993.

FIELD OF THE INVENTION

The present invention is referred to sulphur-acylated derivatives of L-pyroglutamyl-L-cysteine, also denominated 2-(S)-(2-pyrrolidone-5-(S)-carbonylamido)-3-mercaptopropionic acid, which are suitable for the treatment of diseases connected with glutathione deficiency, the process for their preparation, and the pharmaceutical compositions containing same.

PRIOR ART

Glutathione, a universal component of mammals cells, plays a very important role in oxyreductive metabolic processes. In particular, glutathione—active in the reduced form (GSH)—thanks to the presence of the —SH group plays a key role in various cellular defense and repair mechanisms.

For example, GSH is a detoxicant of organic peroxides, free radicals, and endogenous and exogenous toxic agents, the latter being also denominated xenobiotic agents (Flohé L. et al., Glutathione: Metabolism and Function, Arias M. and Jacoby W. B. eds., Raven Press, New York, 115–135, 1978; Bellomo G., Richelmi P. et al., Biochem. Pharmacol., 36, 1313, 1987; Di Monte D. et al., Arch. Biochem. Biophys., 235, 343, 1984) and offers protection against potentially hepatotoxic compounds (ethyl alcohol and some groups of drugs) (Spice H., Parcher C. M., Smith G., Agent Actions, 4, 125, 1974).

At present, reduced glutathione is commercially available in various specialties utilized as detoxicants (e.g. for the treatment of intoxications induced by antineoplastic, antitubercular, neuroleptic, antidepressant drugs and by paracetamol), in the prophylaxis and treatment of damages induced by exposure to X-rays, and in the treatment of alcohol syndrome and associated disorders. Furthermore, as reported in literature (Sies H. and Cadenas E., Biological Basis of Detoxication, Caldwell J. and Jekoby B. eds., San Diego Academic, 1988), a pathological or physiological or experimental deficiency of GSH causes injuries to the involved brain regions.

Recently, evidence has pointed to a considerable involvement of GSH in the immune system of the organism, e.g. by providing cells with the cysteine required to improve their functioning.

It is, therefore, very important to have drugs that increase or restore optimal glutathione concentrations and, consequently, are suitable for the treatment of diseases like psychic fatiguing states, cognitive deficits of the evolutive age, mental deterioration in the elderly, humour disturbances, acute and chronic alcoholism, hepatic diseases following alcohol abuse and intoxication induced by some chemotherapic, antineoplastic, and antitubercular drugs.

Pharmaceutical compositions containing L-pyroglutamyl-L-cysteine, which are suitable for the treatment of cataract in humans and other mammals (Italian patent application No. 19783 A/88) and of states induced by glutathione deficiency (Italian patent application No. 21967 Reg. A) are known.

European patent application No. A2 498 268 is referred to L-pyroglutamic acid derivatives containing either $C_3$–$C_4$ L-amino acids or compounds, such as for example homocysteine thiolactone, having an immunostimulating, antiradicals, antitoxic, antishock, and antiageing action.

DETAILED DESCRIPTION OF THE INVENTION

The present invention is referred to acyl derivatives of L-pyroglutamyl-L-cysteine of formula (I)

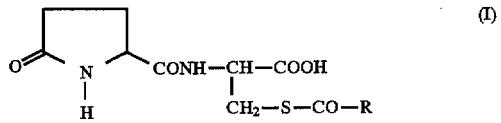

where R is a linear or branched alkyl containing from 1 to 6 carbon atoms, and their pharmaceutically acceptable salts.

The Applicant found that the derivatives of formula I) and the compositions containing same enhance the synthesis of endogenous GSH in vivo, thus modulating the intracellular "oxidative" state. In particular, derivatives of formula (I) were found to enhance the formation of hepatic GSH in vivo more than GSH and their single constituents (5-oxyproline and cysteine) (cf. Test 1) and to be capable of permeating cellular membranes (cf. Test 2).

Compared with GSH, derivatives of formula (I) show a better penetration into the cells and an improved bioavailability after oral administration.

The derivatives of formula (I) are suitable for human therapy, in particular for the treatment of various diseases induced by glutathione deficiency, such as the pathological states related to oxidative tissual damages, in particular imputable to an excess of free radicals. Some examples of diseases caused by glutathione deficiency are: intracellular oxidative states disequilibrium following alcohol abuse, exposure to xenobiotic agents, damages caused by radiations, hepatic diseases, intoxications from drugs and chemical agents, poisonings from heavy metals, physiological brain ageing (e.g. Parkinson's disease, brain degenerations due to decreased glutathione levels caused by altered antioxidant defence mechanisms, such as loss of memory and of the capability of learning) as well as acute and chronic neurodegenerative diseases (e.g., among acute pathologies: acute ischaemic states, in particular cerebral ictus, hypoglycaemia, and epileptic attacks; among chronic pathologies: amyotrophic lateral sclerosis, Alzheimer's disease, Hungtington's chorea), diseases related to an altered functionality of the immune system, in particular tumours immunotherapy, infertility, in particular male infertility. The present derivatives are also suitable for organs reperfusion following ischaemic events mainly imputable to free radicals. Among the derivatives of the present invention, the preferred one has R=$CH_3$, i.e. S-acetyl-L-pyroglutamyl-L-cysteine, hereinafter also referred to as PSC.

The derivatives of formula (I) may be prepared from L-2-pyrrolidone5-carboxylic acid (L-pyroglutamic acid) according to the process represented by the following scheme:

a) Activation of L-pyrrolidone carboxylic acid
b) Preparation of protected L-cysteine amide
c) Removal of —SH group protection
d) Acylation The said process, which is also an object of the present invention, comprises the following steps:

a) treating the L-2-pyrrolidone-5-carboxylic acid with a compound R'OH, preferably in stoichiometric amount, where R' is a phenyl substituted with one or more substituents selected from the group consisting of halogens and nitro-groups, in the presence of a coupling agent, preferably in stoichiometric amount, preferably at a temperature of −10° to +10° C., and more preferably of 0° to 5° C., in an organic polar solvent, to give an ester of formula (II)

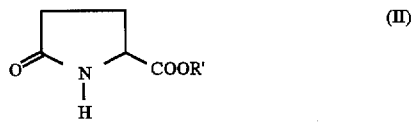

where R' is as defined above, b) treating the ester of formula (II) with L-cysteine derivative of formula (III), preferably in stoichiometric amount

where R" is a protective group of the —SH function, to give an amide derivative of L-pyroglutamic acid of formula (IV)

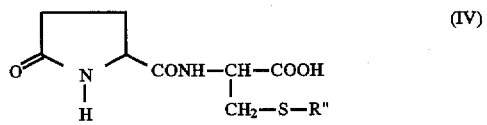

c) removing the sulphur protective group by treatment with a reducing system to give L-pyroglutamyl-L-cysteine of formula (V)

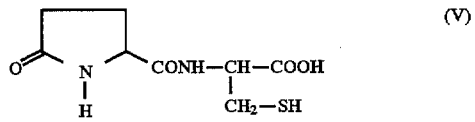

d) acytating L-pyroglutamyl-L-cysteine by treatment with an acylating agent in the presence of an acid or basic catalyst, in a polar solvent, preferably at a temperature of −10° to +10° C., and more preferably of 0° to +5° C., to give the acyl derivative of formula (I).

The attempts made to obtain the derivatives of formula (I) directly by condensation of the L-pyroglutamic acid ester of formula (II) with sulphur-acylated L-cysteine did not give satisfactory results, due to the trans-acylation processes taking place at the operative conditions adopted for the formation of the amidic bond of dipeptide (IV).

Furthermore, the attempts made to carry out the final acylation with excess pyridine as a solvent brought about low yields and unsatisfactory results, a complete removal of residual pyridine from the reaction product being hardly possible.

The R'OH compounds that may be used in step a) are the phenols commonly utilized for activating the carboxylic group in protein syntheses, e.g. pentachlorophenol, p-nitrophenol, and 2,4-dinitrophenol.

The polar solvent that may be used in steps a) and b) may be selected among dimethylsulphoxide, dimethylformamide and dioxane, preferably dimethylformamide.

The coupling agent used is typically dicyclohexyl carbodiimide. The ester of formula (II) obtained in step a) may be crystallized, once or repeatedly, from halogenated organic solvents, ethers, esters, hydrocarbons and mixtures thereof. A preferred embodiment of the present invention envisages a first crystallization from a CHCl₃-petroleum ether mixture and a second crystallization from ethyl acetate. Step b) may be carried out as disclosed in J. Chem. Soc., 1960, 1390–1393.

As far as the selection of the R" group in protected L-cysteine is concerned, it is to be stressed that the expression "protective group of the —SH function" is used herein to average value a group commonly utilized in peptide syntheses to protect the thiol groups and which is, at the same time, stable under the conditions of amidic bond formation adopted in the subsequent step.

Groups meeting the aforesaid requirements are for example the benzyl group or the mercaptide residue derived from L-cysteine, i.e. the NH₂—CH(COOH)CH₂S- residue, the benzyl group being preferred. Protected L-cysteine of formula (III) is a commercially available product and, in any case, may be prepared according to the method described in J. Chem. Soc., 1960, 390–1393.

The product of formula (IV) obtained as described in b) may be purified by crystallization from alcohols, preferably from absolute ethanol.

The expression "reducing system" is herein used to average value any system commonly used by those skilled in the art for the reductive cleavage of sulphur protecting groups, such as for example Na in liquid NH₃ or H₂ in the presence of Pd on carbon as a catalyst. Step c) may be carried out according to the disclosures in Biochem. Prepar., 2, 87 (1952).

L-pyroglutamyl-L-cysteine obtained in c) is conveniently crystallized from an alcohol, such as methanol.

In step d) the acylating agent is selected among acylating substances known to those skilled in the art, such as for example carboxylic acids anhydrides, mixed anhydrides obtained from carboxylic acids and halogencarbonates, such as ethyl chloroformate, and acyl halides, particularly acyl chlorides.

Preferred acylating agents are the anhydrides, particularly acetic anhydride.

Acylation may be carried out in the presence of acid catalysts, e.g. sulphuric acid, and of basic catalysts, e.g. sodium bicarbonate and triethylamine.

The preferred catalyst is sodium bicarbonate.

The acyl derivative of formula (I) obtained as per d) may be purified by chromatography, preferably by ion exchange chromatography on Dewex-1 (CH₃COO⁻), eluting with 1 N acetic acid, freeze-drying the fractions containing product (I), or by crystallization from polar solvents, such as alcohols, preferably ethanol, after extraction with n-butanol and washing of butanol extracts with water.

The derivatives of formula (I) of the present invention may be advantageously prepared according to an alternative process, comprising the following steps:

a') treating L-2-pyrrolidon-5-carboxylic acid with an L-cysteine ester of formula (VI):

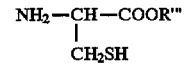

wherein R'" is the residue of the protecting group of a carboxylic function, in an inert organic solvent, in the presence of a coupling agent;

b') hydrolyzing the ester group contained in L-pyrroglutammyl-L-cysteine

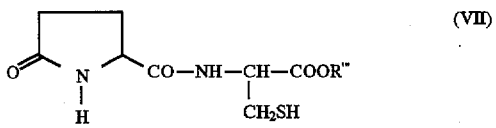

(VII)

obtained in the preceding step, wherein R'" has the above mentioned meaning, by reacting this compound with an organic or inorganic base in the presence of water, and subsequently acidifying the reaction mixture;

c') reacting L-pyroglutamyl-L-cysteine of formula (VII), coming from the preceding step, with an acylating agent, in the presence of an acid or a basic catalyst, in a polar solvent.

R'" is the residue of any ester function utilized in organic chemistry to protect the carboxy group, provided that it is compatible with the other functional groups present in the molecular structure of the compounds of formula (VI) and (VII) and that it is stable at the operating conditions of step a').

In particular and for merely illustrative purposes, R'" may be a linear or branched alkyl group of from 1 to 6 carbon atoms, a 3–10 membered alicyclic group on a 6–10 membered aromatic group.

All these groups may, on their turn, be substituted with other groups, for example with from 1 to 3 groups selected from the group consisting of: linear or branched alkyl radicals of from 1 to 6 carbon atoms, linear or branched alkoxy radicals of from 1 to 6 carbon atoms, halogen atoms, 6–10 membered aromatic residues.

The above mentioned R'" alkyl or alicyclic groups may also contain one or more ethylenic or acetylenic unsaturations.

Among the alkyl groups we may mention: methyl, ethyl, isopropyl; among the alkyl groups substituted with aromatic groups: the benzyl residue; among the alicyclic groups we may cite cyclohexyl, among the aromatic groups phenyl, biphenyl, α- and β-naphtyl residue, the structural isomers of chlorophenyl residue such as 2,3 or 4-chlorophenyl are to be mentioned.

Preferably, R'" is a $CH_3$ group. The derivative of formula (VI), having R'"=$CH_3$ is a commercially available product.

Other L-cysteine esters to be used in the above described process may be prepared by following conventional synthetic methods. In step a') aprotic solvents such as dimethylsulfoxide, dimethylformamide, dioxane, and ethyl acetate, halohydrocarbons such as chloroform, methylene chloride or any possible mixture of thereof, may be used as the inert organic solvent. Preferably, dimethylformamide is used.

Any compound known to the skilled man to facilitate the amidic or estereal bond formation may be advantageously used as the coupling agent (see in this regard J. March, "Advanced Organic Chemistry", John Wiley & Sons, 3rd Ed. 1985, pages 372–374 and pages 349–350). Dicyclohexylcarbodiimide is preferably used.

Step a') is generally carried out at a temperature ranging from −40° to +70° C., preferably from −10° to +10° C.

The derivative of formula (VI) may be used in step a') in the form of a salt, particularly the corresponding salt with an acid, such as the hydrochloride salt, and, in this case, in the is carried out in the presence of a base which may be a tertiary aliphatic amine such as trimethylamine, a tertiary aromatic amine such as N,N-dimethylaniline, or a heterocyclic base such as pyridine. In preferred conditions, triethylamine is used.

The product coming from step a') may be purified by crystallization, in particular from an alcohol such as methanol.

Step b') can be carried out only in water, or using water in admixture with a number of cosolvents, such as dioxane, dimethylformamide, alcohols, as for example methanol. Mixtures containing water and one or more cosolvents in all proportions can be used (for example, mixtures methanol: water in a volumetric ratio 99:1). Hydroxides, carbonates or bicarbonates of alkali- or alkali-earth metals and of ammonium (for example NaOH, $Na_2CO_3$, $NaHCO_3$, $NH_4OH$) may be used as the inorganic base.

Tertiary aliphatic or aromatic amines, such as triethylamine and N,N-dimethylaniline, or hetercyclic aromatic bases, such as pyridine and N,N-dimethylaminopyridine may be used as the organic base, alone or in admixture. Preferably $NaHCO_3$ is used.

Step b') can be carried out at a temperature of from +20° to +70° C. for a time period of from 2 to 16 hours.

L-pyroylglutammyl-L-cysteine is advantageously recovered from the reaction mixture by acidifying to pH 2–3, then it is separated from the inorganic salts by dissolving it in an organic solvent for example an alcohol such as ethanol, then it is precipitated by the addition of an other solvent selected from the group consisting of acetone, methylethylketone, ethyl acetate, preferably ethylacetate. The product may be also recrystallized from alcohol for example isopropanol.

As far as step c') is concerned, the same considerations are to be made relating to step d) of the first process, previously described. The alternative process just described affords derivatives (I) in large yields and with a high purity level. The process is particularly advantageous in so far as it can be accomplished with only three steps starting from commercially available starting materials. In particular, in this process both the activation of the carboxy group, and the protection of the thiol group, requiring consequently a further step of remotion of the protecting group, are no necessary.

The present invention also relates to the therapeutic compositions containing, as active ingredient, an effective dose of at least one derivative of formula (I) or of a pharmaceutically acceptable salt thereof, in combination with pharmaceutically acceptable excipients. The said compositions are suitable for human therapy, in particular for the treatment of the aforesaid diseases induced by glutathione deficiency.

To achieve the desired therapeutic effects, the product may be administered to patients by various routes, e.g. orally or parenterally, in the pure form or in the form of pharmaceutical compositions.

The formulations of suitable pharmaceutical compositions may be obtained on the basis of known techniques, such as those described in "Remington's Pharmaceutical Sciences Handbook", Hack Publishing Co., U.S.A.

The amount of product administered by the oral route may vary from 5 mg/kg/die to 50 mg/kg/die, preferably from 7 mg/kg/die to 30 mg/kg/die.

The amount of active ingredient administered by the parenteral route may vary from 1 mg/kg/die to 30 mg/kg/die, preferably from 5 mg/kg/die to 20 mg/kg/die.

The amount of active ingredient in a dosage unit for oral administration may be e.g. of 100 to 3000 mg and in a dosage unit for parenteral administration e.g. of 30 to 2000 mg.

The compositions according to the invention are averagely administered once or twice a day; however, more frequent administrations may be, at least in some cases, appropriate and their number may vary with the patient's physical status and the route of administration used.

For oral administration, the compound may be formulated in solid or liquid formulations, in the form of capsules, pills, tablets, powders, solutions, suspensions of emulsions, optionally in sustained release forms, etc.

A solid dosage unit may be a soft or hard gelatin capsule containing inert excipients and lubricants such as lactose, saccharose or starch.

The compounds of the invention may be also formulated in the form of tablets using conventional excipients, such as lactose, saccharose, starch, gelatin, alginic acid, stearic acid, magnesium stearate, etc.

For parenteral administration, the compounds of formula (I) may be administered as injectable formulations, and may be therefore dissolved or suspended in pharmacologically acceptable diluents, with a vehicle that may be sterile such as water or an oil, with or without addition of other components.

The oils that may be used aye vegetable of mineral of synthetic type, such as peanut oil, soybean oil, mineral oil.

The vehicles for the injectable solutions are generally water, aqueous solutions of mineral salts, aqueous solutions of dextrose or of other sugars, ethanol, glycols, e.g. propylene or polyethylene glycols.

The compositions which are object of the present invention may contain, in addition to the aforesaid excipients and active ingredient, other active ingredients exerting a complementary or in any case useful action.

The following examples are reported for purpose of illustrating without limiting the present invention.

EXAMPLE 1

Preparation of 2-(S)-(2-pyrrolidone-5-(S)-carbonyl amido)-3-acetylmercapto propionic acid a) Preparation of pentafluorophenyl-L-pyroglutamate A solution of 40 g of L-pyroglutamic acid (0.31 mols) and 83.16 g of pentachlorophenol (0.31 mols) in 530 ml of dimethylformamide (DMF) was added at 0° C. with a solution of 64 g of dicyclohexyl carbodiimide (0.31 mols) in 62.2 ml of DMF. The mixture was allowed to react for 16 hrs at room temperature with stirring. The reaction mixture was filtered to eliminate the dicyclohexylurea formed and the filtrate was evaporated to dryness (40° C., 0.5–1 mmHg) (66.66 –133.32 Pa) yielding a residue of 97 g. Said residue was taken up with $CHCl_3$ and concentrated until crystallization start. Petroleum ether (3–4 vols., 40°–70°) was added and the mixture was allowed to stand overnight at 10° C. The precipitate was filtered yielding a residue of approx. 80 g; said residue, crystallized from ethyl acetate, gave 60.41 g of crystals (needles). M.p. 180°–184° C.

$^1$H-NMR, 80 MHz, deutero-DMSO: δ 8.33 (s, 1H, =NH), 4.68 (m, 1H, 2 —CH), 2.27 (m, 4H, 3 —$CH_2$ and 4 —$CH_2$).

b) Preparation of L-pyroglutamyl-S-benzyl-L-cysteine 7.10 g of pentachlorophenyl-L-pyroglutamate (0.0189 mols), 4 g of S-benzyl-L-cysteine (0.0189 mols) and 6 ml of triethylamine in 100 ml of dimethylformamide (DMF) were left under stirring for 24 hrs at room temperature, sheltered from light. The mixture was filtered for insoluble elimination and the filtrate was evaporated to dryness (40° C., 0.5–1 mmHg). (66.66–133.32 Pa); the oily residue was taken up with 250 ml of $CH_2Cl_2$, the resulting solution was extracted with water (3×200 ml) while the emulsion formed, if any, was separated by centrifuging. The aqueous phase was acidified up to the Congo red color change and extracted with 1 l of n-butanol (4×250 ml).

The butanol phase was treated with 10 g of anhydrous sodium sulphate and the filtrate, evaporated to dryness, gave a residue of 4.03 g; said residue was taken up with abs. ethanol, decolourized on activated carbon, and the filtrate was evaporated to dryness. The residue was crystallized from abs. ethanol and gave 2.1 g of chromatographically (TLC) pure L-pyroglutamyl-S-benzyl-L-cysteine crystals (needles). M.p. 181°–183° C.

$^{13}$C-NMR, 200 MHz, $CD_3OD$: δ 181.94 (5' —C=O), 175.32 (COOH), 173.80 (1' —C=O), 139.55 (quaternary aromatic), 130.25 (β-aromatic carbons), 129.71 (α-aromatic carbons), 128.31 (gamma-aromatic carbon), 58.05 (2' —C), 52.95 (2' —C), 36.91 ($CH_2$-benzyl), 33.70 (3 —$CH_2$), 30.36 (4' —$CH_2$), 26.83 (3' —$CH_2$).

c) Debenzylation of L-pyroglutamyl-S-benzyl-L-cysteine

Liquid $NH_3$ (150 ml) kept under stirring and in a nitrogen environment was added lotwise with approx. 310 mg of metallic sodium until the colour turns blue. This solution was added with 1.5 of L-pyroglutamyl-S-benzyl-L-cysteine and the resulting mixture was left under stirring until complete decolourization.

Twenty minutes later, ammonia was removed by evaporation under a nitrogen stream, the residue was added with 300 ml of water, and the solution was acidified with conc. HCl to pH 1. The resulting solution was extracted with 1l of butanol (4×250 ml) and the butanol extracts were evaporated to dryness under vacuum.

The residue (1.346 g) was added with water and the suspension was filtered to eliminate the insoluble oily fraction and evaporated to dryness to give 1.109 g of a solid product. After crystallization from MeOH, 460 g of L-pyroglutamyl-L-cysteine were obtained.

The assigned structure was confirmed by IR, UV and mass spectroscopy, and by the NMR analyses reported below:

$^1$H-NMR, 80 MHz, $CD_3OD$ (TMS): δ 2.36 (m, 4H, 3' —$CH_2$, 4' —$CH_2$), 3.02 (m, 2H, 3 —$CH_2$), 4.31 (t, 1, 2' —CH), 4.63 (dd, 1H, 2 CH).

$^{13}$C-NMR, 200 MHz, $CD_3OD$ (TMS): 181.9 ppm (s, 5' —C=O), 174.41 (s, COOH), 172.16 (s, 1' —C=CO), 57.07 (d, 2 —C), 55.01 (d, 2' —C), 29.5 (t,4' —C), 25.61 (t, 3 —C), 25.08 (t, 3' —C).

d) Acetylation of L-pyroglutamyl-L-cysteine

An aqueous solution (160 ml) containing 1.173 g of L-pyroglutamyl-L-cysteine and 1.07 g of sodium bicarbonate was added, at 0° C. and under stirring, with 26.7 ml of acetic anhydride. The resulting mixture was maintained under said conditions for 15 min. The reaction mixture was stirred for an additional 15 min. at room temperature and then evaporated to dryness under vacuum. The residue was added with water and purified by ion exchange chromatography on Dowex-1 ($CH_3$—$COO^-$), eluting with 1N acetic acid. The fractions that contained the desired product were combined and freeze-dried to give a residue of 1.25 g.

This process may be modified as follows: the residue was added with water (acidified with HCl to pH 3) and extracted with 6 portions of n-butanol; the organic extract was washed with 2 portions of water and concentrated.

The residue, taken up with ethanol, gave 1 g of product. M.p. 115°–117°.

A sample recrystallized from ethanol gave a product with m.p. of 130°–132° C.

The spectroscopic data ($^1$H-NMR and $^{13}$C-NMR) confirmed the structure assigned.

$^{13}$C-NMR, 200 MHz, $CD_3OD$ (TMS): δ 203 ppm (s, —C=O), 185 ppm (s, —C=O), 179 ppm (s, —COOH), 176.2 ppm (s, —C=O), 60 ppm (d, —CH), 55.2 (d, —CH), 33.6 (t, 33.6), 32.05 ppm (t, —CH), 28.05 ppm (t, —CH).

EXAMPLE 2 a') 0.29 mol L-cysteine-methylester hydrochloride are reacted in 100 ml dimethylformamide, previously cooled to −0°−+5° C., with 0.30 mol triethylamine. 0.29 mol of L-pyroglutamic acid are then introduced and a solution of dicyclohexylcarbodiimide (0.32 mol) in 60 ml dimethylformamide is added drop by drop, while cooling the reaction mixture with an ice-bath.

When the addition of the coupling agent is completed, the mixture is left to react for 24 hours, and the formed precipitate is then filtered. Mother liquors are concentrated to small volume, thereby obtaining an oil which is dissolved in hot alcohol (methanol). The solution is left to cool spontaneously to room temperature, in this way L-pyroglutamyl-L-cysteine methyl ester precipitates in the form of a white crystalline product, which is filtered under vacuum, with 3×10 ml methanol.

b') An aqueous solution of 0.058 mol of L-pyroglutamyl-L-cysteine methyl ester is reacted with 0.050 mol $NAHCO_3$. The mixture is then heated to a temperature comprised between 20° and 70° C. for a period comprised between 2 and 16 hours. The reaction mixture is then cooled and filtered. The solution thus obtained is concentrated under vacuum to small volume and acidified with 1N HCl to pH 2–3. The semisolid product is then added with 20 ml hot ethanol, cooled and filtered. The obtained solution is then percolated in 200 ml ethyl acetate.

A precipitate forms, which after filtration and washing affords 7 g of a product. This product is then recrystallized from isopropanol and chromatographically pure L-pyroglutamyl-L-cysteine (TLC) is obtained.

c') The acylation reaction is carried out following the same operating conditions described in step d) of Example 1.

Pharmaceutical compositions containing 2-(S)-(2-pyrrolidone-5-(S)-carbonyl amido)-3-acetyl mercapto propionic acid

1. FORMULATIONS FOR INJECTION

One vial contains

| | | | | |
|---|---|---|---|---|
| (I) (R = $CH_3$) | 100 mg | 600 mg | 1000 mg | 2000 mg |
| sodium metabisulphite | 2 mg | 4 mg | 5 mg | 10 mg |
| apyrogenous sterile water q.s. to | 2 ml | 4 ml | 5 ml | 10 ml |

Freeze-dried product
One vial contains

| | | | | |
|---|---|---|---|---|
| (I) (R = $CH_3$) | 300 mg | 600 mg | 1000 mg | 2000 mg |
| water for injectable compositions | 3 ml | 4 ml | 5 ml | 10 ml |

2. ORAL FORMULATIONS

Tablets
One tablet contains

| | | |
|---|---|---|
| (I) (R = $CH_3$) | 200 mg | 400 mg |
| starch | 80 mg | 70 mg |
| microgranular cellulose | 86 mg | 56 mg |
| precipitated silica | 5 mg | 7 mg |
| carboxymethylcellulose | 20 mg | 25 mg |
| talc | 6 mg | 7 mg |
| magnesium stearate | 3 mg | 5 mg |

Capsules
One capsule contains

| | | |
|---|---|---|
| (I) (R = $CH_3$) | 200 mg | 400 mg |
| microcrystalline cellulose | 20 mg | 40 mg |
| precipitated silica | 4 mg | 8 mg |
| magnesium stearate | 2 mg | 4 mg |

Pharmaceutical compositions containing 2-(S)-(2-pyrrolidone-5-(S)-carbonyl amido)-3-acetyl mercapto propionic acid Bottles per os
One bottle per os contains

| | | |
|---|---|---|
| (I) (R = $CH_3$) | 1000 mg | 1500 mg |
| 70% sorbitol solution | 2 g | 2 g |
| glycerol F.U. | 1.5 mg | 1.5 mg |
| saccharine | 8 mg | 12 mg |
| methyl p-oxybenzoate | 15 mg | 22.5 mg |
| propyl p-oxybenzoate | 5 mg | 7.5 mg |
| tangerine flavouring | 40 mg | 50 mg |
| purified water q.s. to | 10 ml | 15 ml |

Sachets
One sachet contains

| | |
|---|---|
| (I) (R = $CH_3$) | 3000 mg |
| mannite | 6900 mg |
| lemon flavouring | 100 mg |

The pharmaceutical compositions of this invention enhance glutathione synthesis in vivo and in vitro. The data reported in Table 1 indicate that the claimed compositions possess a better activity than GSH and a protective effect in rats whose GSH had been experimentally reduced.

PHARMACOLOGICAL TESTS

GLUTATHIONE PRODUCTION TESTS

TEST No. 1
Protection from ethanol acute administration

Comparison with glutathione (GSH), with 2-oxy-L-proline (O-PRO) and with L-cysteine (CIS).

Male albino Wistar rats weighing between 180 and 230 g were used. All animals were fasted for 24 hours prior to administration of isotonic solution, ethanol or ethanol combined with the test substances.

As concerns the test substances, rats were intraperitoneally (i.p.) injected with compound of formula I (R=$CH_3$) at doses of 10, 30, and 50 mg/kg and, for purposes of comparison, with the single constituents of compound (I) (R=$CH_3$), 5-oxy-L-proline (O-PRO) and L-cysteine (CIS), both at a 50 mg/kg dose.

One hour after administration of the test substance, ethanol was injected i.p. at the dose of 3 g/kg.

Thirty minutes later, the animals were sacrificed by decapitation and their liver was excised. GSH was determined by homogenization in the presence of 2% β-mercaptoethanol and centrifuging and evaluated according to the method described by O. Orwar et al., J. Chromatogr., 556, 39–55 (1991).

The results obtained are listed in Table 1.

TABLE 1

| Treatment | Dose | GSH Content |
|---|---|---|
| isotonic solution | | 6.7 ± 2.1 |
| ethanol | 3 g/kg | 1.5 ± 0.4 |
| ethanol + (I) (R = $CH_3$) | 3 g + 10 mg/kg | 3.6 ± 0.3 |
| ethanol + (I) (R = $CH_3$) | 3 g + 30 mg/kg | 4.3 ± 0.6 |
| ethanol + (I) (R = $CH_3$) | 3 g + 50 mg/kg | 5.8 ± 0.4 |
| ethanol + GSH | 3 g + 50 mg/kg | 3.5 ± 0.6 |
| ethanol + O-PRO | 3 g + 50 mg/kg | 3.4 ± 0.3 |
| ethanol + CIS | 3 g + 50 mg/kg | 2.7 ± 0.3 |

Administration of derivative (I) (R=$CH_3$) to ethanol-treated rats enhances hepatic glutathione formation nearly to physiological levels and, in any case, to levels higher than those obtained with 5-oxy-L-proline or L-cysteine.

TEST No. 2

Effect of ethanol chronic treatment on GSH concentration in main organs.

GSH contents in liver, skin, brain, lungs and heart were determined on groups of male albino Wistar rats (No. 9) treated with product (I) (R=CH$_3$) per os, at a daily dose of 50 mg/kg, and with ethanol (7% solution in drinking water) in respect of a group of animals treated with ethanol alone.

The animals were sacrificed three weeks later.

GSH was determined according to the method of Test 1. The results obtained are listed in Table 2.

TABLE 2

| Treatment | No. of animals | | GSH (µM/g tissue) |
|---|---|---|---|
| Controls | 9 | liver | 5.08 ± 1.0 |
| | | skin | 6.10 ± 0.8 |
| | | brain | 2.80 ± 0.7 |
| | | lungs | 2.05 ± 0.6 |
| | | heart | 3.90 ± 0.6 |
| ethanol | | liver | 1.85 ± 0.5* |
| | | skin | 2.25 ± 0.8* |
| | | brain | 2.00 ± 0.6 |
| | | lungs | 1.08 ± 1.1 |
| | | heart | 1.01 ± 0.3* |
| ethanol + 50 mg of (I) (R = CH$_3$) | | liver | 5.00 ± 0.8** |
| | | skin | 4.90 ± 0.7 |
| | | brain | 2.52 ± 0.3 |
| | | lungs | 2.30 ± 0.5 |
| | | heart | 2.80 ± 0.6 |

*$P < 0.05$;
**$P < 0.01$

Tests in vitro

Test substance: S-acetyl-L-pyroglutamyl-L-cysteine (I) (R=CH$_3$).

The experimental model envisages the isolation of hepatic parenchymal cells of rats following perfusion, with collagenase, of the isolated organ. Prior to each test, hepatocytes vitality was quantified by Tripan Blue extrusion. Only the cells with a vitality greater than 90% were utilized. Hepatocytes were resuspended, at a concentration of 106 cells/ml, in a saline medium (Krebs Heinseleit) at ph 7.4, and then placed into rotating flasks in the presence of O$_2$ (95%) and CO$_2$(5%), at 37° C. Cells keep vital for 5–6 hours at least.

The cells were pretreated with diethylmaleate (DEM), which causes a significant reduction in the GSH levels of hepatocytes, to levels of about 25% in respect of those of normal hepatocytes. The cells were then washed for 30 min. and incubated with various concentrations of the test substance (from 0.25 to 5 mM).

By this experimental model it is possible to test the effect of the substance by evaluating the hepatic functionality determined by measurements of the vitality (Tables Nos. 3, 4, and 5) and of glutathione content (Tables 6, 7, and 8).

In the Tables 3–8 herein below reported, the controls are represented by normal hepatocytes, not treated either with DEM or with compound (I).

TABLE 3

Cells vitality after treatment with 0.25, 0.5, 2.5 mM of derivative (I) (R = CH$_3$)
The results are expressed as a percentage in respect of controls.

| | 0 time | 30 min | 1 hr | 2 hrs | 4 hrs |
|---|---|---|---|---|---|
| 0.25 mM | 100 | 101 | 98 | 100 | 116 |
| 0.50 mM | 100 | 101 | 100 | 101 | 114 |
| 2.5 mM | 100 | 94 | 95 | 95 | 104 |

TABLE 4

Cells vitality after treatment with diethylmaleate (DEM) and incubation with 0.25 and 0.5 mM of derivative (I) (R = CH$_3$)
The results are expressed as a percentage in respect of controls.

| | 0 time | 30 min | 1 hr | 2 hrs | 4 hrs |
|---|---|---|---|---|---|
| DEM | 95 | 95 | 93.4 | 91 | 92 |
| DEM + 0.25 mM | 95 | 90 | 87 | 86 | 87 |
| DEM + 0.50 mM | 95 | 88 | 85 | 84 | 85 |

Cells vitality after treatment with diethylmaleate (DEM) and incubation with 1, 2.5 and 5 mM of derivative (I) (R=CH$_3$)

TABLE 5

Cells vitality after treatment with diethylmaleate (DEM) and incubation with 1, 2.5, and 5 mM of derivative (I) (R = CH$_3$)
The results are expressed as a percentage in respect of controls.

| | 0 time | 30 min | 1 hr | 2 hrs. | 4 hrs |
|---|---|---|---|---|---|
| DEM | 96 | 92 | 92 | 94 | 95 |
| DEM + 1.0 mM | 96 | 92 | 90 | 89 | 88 |
| DEM + 2.5 mM | 96 | 89 | 84 | 83.5 | 82 |
| DEM + 5.0 mM | 96 | 88 | 84 | 82 | 80 |

TABLE 6

Glutathione concentrations (nmol/10$^6$ cells) after treatment with diethylmaleate (DEM) and incubation with 1, 2.5, and 5 mM of derivative (I) (R = CH$_3$)
The results are expressed as a percentage in respect of controls.

| | 0 time | 30 min | 1 hr | 2 hrs | 4 hrs |
|---|---|---|---|---|---|
| DEM | 22.7 | 22.7 | 31.6 | 41.7 | 53.3 |
| DEM + 1.0 mM | 25.8 | 52.7 | 71.0 | 96.7 | 118.9 |
| DEM + 2.5 mM | 23.9 | 61.1 | 89.0 | 118.9 | 172.7 |
| DEM + 5.0 mM | 26.6 | 69.4 | 92.0 | 118.9 | 190.9 |

TABLE 7

Glutathione concentrations (nmol/10$^6$ cells) after treatment with diethylmaleate (DEM) and incubation with 0.25 and 0.5 mM of derivative (I) (R = CH$_3$)
The results are expressed as a percentage in respect of controls.

| | 0 time | 30 min | 1 hr | 2 hrs | 4 hrs |
|---|---|---|---|---|---|
| DEM | 30.0 | 31.4 | 38.7 | 40.6 | 56.9 |
| DEM + 0.25 mM | 28.0 | 42.8 | 54.8 | 81.2 | 83.0 |
| DEM + 0.50 mM | 28.4 | 45.7 | 74.2 | 103.0 | 138.4 |

TABLE 8

Glutathione concentrations (nmol/$10^6$ cells) after treatment with
0.25, 0.50, and 2.5 mM of derivative (I) (R = $CH_3$)
The results are expressed as a percentage in respect of controls.

| | 0 time | 30 min | 1 hr | 2 hrs | 4 hrs |
|---|---|---|---|---|---|
| 0.25 mM | 104 | 117 | 133.5 | 142 | 146 |
| 0.50 mM | 107 | 144 | 154.8 | 159 | 207 |
| 2.5 mM | 99.5 | 158 | 181.6 | 191 | 210.9 |

The following conclusions have been drawn or hypothesized from the above results.

S-acetyl-L-pyroglutamyl-L-cysteine, even at high concentrations (up to 5 mM), does not cause cellular toxicity and, at least in vitro, is very well tolerated.

The test substance causes an increase in GSH basal values in normal hepatocytes (not treated with DEM), said increase being significant at concentrations from 0.5 mM (greater than 180% after 4 hrs in respect of controls). This clearly indicates the permeability of the hepatocyte membrane to S-acetyl-L-pyroglutamyl-L-cysteine (Table 8).

In normal hepatocytes, S-acetyl-L-pyroglutamyl-L-cysteine concentrations of 2.5 mM cause an increase, after 4 hrs, in basal GSH to an extent that is superimposable to that caused by concentrations five times lower (0.5 mM) (Table 8). This result would suggest a saturable mechanism of substance active transport inside the cells.

In isolated DEM-pretreated hepatocytes (GSH levels of about ¼ in respect of normal-hepatocytes), the susbtance causes an increase in GSH values, which, for low concentrations, is dose-related (about 80% for 0.25 mM, about 130–140% for 0.5 mM) (Table 7, 4 hours). At higher concentrations, the increase in the GSH content is still detectable at 1 mM (about 120%); instead, concentrations of 2.5 and 5 mM always produce the same effect (greater than 170%) (Table 6). This finding might confirm the result obtained with DEM non-pretreated hepatocytes, thus strengthening the hypothesis of an active and, therefore, saturable transport of the substance.

In the hepatocytes treated with DEM and then tested with derivative (I) (R=$CH_3$), a cellular suffering (cellular dilatation without appearance of vesicles) was at first detected, which disappeared after few tens of minutes. The hypothesis may be ventured that said effect may be due to the "effort" to uptake derivative (I) (R=$CH_3$) by GSH-deficient cells.

TEST No. 4
Tests in vivo
Test substance: S-acetyl-L-pyroglutamyl-L-cysteine (derivative (I) (R=$CH_3$))

A test was carried out in vivo on four groups of four rats each, using, as a toxic substance, dichloropropane (DCP), the main constituent of several solvents. DCP is noxious both by ingestion and inhalation and has a notable toxicity to the liver, mediated by an almost total depletion of thiol groups, including those of GSH.

Two substances which are known to be active in treating said intoxication, N-acetyl-L-cysteine (NAC) and glutathione (Tationil[R]) were used as positive controls.

The experimental model involves the study of the effect of DCP toxicity in the rat, in respect of glutathione (GSH) concentration in the main target tissue: the liver.

Tests were carried out on four groups of rats. The first group of animals was administered 2 ml DCP/kg dissolved in oil (40% v/v) per os. Twenty-four hours after DCP administration, blood samples were taken for SGPT measurement, while the animals were sacrificed; small portions of liver were then excised and immediately deproteinized by homogenization in 6% PCA. The chromatographic analyses of GSH and GSSG (oxidized glutathione) were performed.

The second group of animals was treated with the test drug (600 mg/kg i.p.) two hours after DCP administration. The third and fourth groups were treated with N-acetylcysteine (NAC) (250 mg/kg i.p.) and, respectively, with glutathione (Tationil[R]) (600 mg/kg i.p.).

An evaluation of the protective action of the test drug in respect of glutathione involvement in hepatic protection mechanisms was thus possible.

TABLE 9

Test in vivo
GSH nmol/mg protein

| Animals | Control | DCP | DCP + (I) (R = $CH_3$) (600 mg/kg) | DCP + Tationil (600 mg/kg) | DCP + NAC (250 mg/kg) |
|---|---|---|---|---|---|
| 1 | 15 | 2.8 | 2.6 | 1.8 | 2.0 |
| 2 | 16 | 2.1 | 2.4 | 1.3 | 2.9 |
| 3 | 16.3 | 2.3 | 2.6 | 1.4 | 2.3 |
| 4 | 16.5 | — | 3.4 | 1.8 | — |
| average values | 15.9 | 2.4 | 2.7 | 1.6 | 2.4 |

TABLE 10

GPT(U/l)

| Animals | Control | DCP | DCP + (I) (R = $CH_3$) (600 mg/kg) |
|---|---|---|---|
| 1 | 17.2 | 45.6 | 24.4 |
| 2 | 25.4 | 47.4 | 26.4 |
| 3 | 19.0 | 46.5 | 17.4 |
| 4 | 23.7 | — | 20.1 |
| average values | 21.3 | 46.5 | 22.0 |

—: dead

The following conclusions were drawn or hypothesized from the above results.

Death rate of animals treated with DCP alone equalled 25% whereas no death occurred in animals treated also with S-acetyl-L-pyroglutamyl-L-cysteine (derivative (I) (R=$CH_3$)) (Table 9). DCP-treated animals also showed behavioural (torpor) and postural (ataxia) disorders, whereas the animals treated with the test substance did not show any notable modification of said parameters. By macroscopic examination, the liver of the animals treated with DCP alone showed gross degenerative alterations, whereas the animals treated with the test substance showed liver parenchyma within standard limits.

By an extemporaneous and merely qualitative examination, the animals treated with DCP showed evident coagulative disorders, which were absent in the animals treated also with derivative (I)(R=$CH_3$).

Serum GPT analysis proved that said hepatic functionality index was maintained within standard limits by the test substance. Instead, the GPT of DCP-treated animals increased to pathological levels (controls 21.3 U/l, DCP 46.5 U/l, DCP +(I)(R=$CH_3$) 22.0 U/l).

The test substance, like GSH and N-acetyl-L-cysteine, could not normalize the values of hepatic GSH. This fact might be explained by the massive consumption of thiol groups induced by DCP as well as by the long interval between animals intoxication and sacrifice. The results obtained show that, in vitro, the test substance (S-acetyl-L-pyroglutamyl-L-cysteine) is greatly effective in restoring thiol groups and in particular GSH.

A highly interesting hypothesis, which may be inferred from some results obtained in vitro, concerns the intracellular active transport of said-substance: according to this hypothesis, $(I)(R=CH_3)$ would be positively different from GSH.

IMMUNOLOGICAL TESTS

MATERIALS AND METHODS

Animals

Sprague-Dawley rats (Charles River, Calco (CO)), aged 10 weeks (young adults) and 24 months (old), were stabled under standard conditions (24°±1° C., 12 h light/dark cycle, free access to food and water). Handlings were made in such a way as to avoid stressful stimuli.

The animals were stabled in groups of 6 per cage and treated for 2 weeks (15 days) with a PSC daily dose of 600 mg/kg by intraperitoneal route (i.p.).

The following assays were conducted to evaluate the immunostimulating activity of the compound:

1) immunization versus erythrocytes;
2) blastization with concavaline A (ConcA) on splenocytes;
3) blastization with concavaline A (ConcA) and phytohaemagglutinin (PHA) on peripheral lymphocytes;
4) measurement of interleukin-2 (IL-2) production.

All aforesaid assays were carried out on both young and old animals.

Tests in vivo

Immunization tests versus ram erythrocytes in Sprague-Dawley rat immunodepressed by cyclophosphamide (CTX)

0.3 Milliliters of ram erythrocytes (3%) in 0.9% sodium chloride solution were injected to Sprague-Dawley rats, both young (aged 10 weeks, weighing 150–200 g) and old (aged 24 months). A second injection was made on the 21st day after the first one. The rats were treated with PSC (600 mg/kg i.p.). Treatment started 3 days before immunization and continued until the 40th day of experiment. Cyclophosphamide (CTX) (150 mg/kg/die) was injected i.p. on the 3rd, 4th, and 5th day after immunization with erythrocytes.

The animals were subdivided (6 animals each group) into the following experimental groups:

1) Non-immunized controls (CTRL);
2) Immunized controls (CTRL);
3) Immunized +CTX;
4) Immunized +CTX+PSC (600 mg/kg i.p.).

The determination of serum antibodies levels was carried out by agglutination reaction: the serum in 0.9% sodium chloride solution was diluted from 1:2 to 1:1024 and ram erythrocytes at a concentration of $5\times10^8$/ml were added. The determination of antibodies was carried out 2 hrs after incubation at 37° C. Each sample was assayed twice (Tables 11 and 12).

TABLE 11

Effect of PSC i.p. treatment on immunization with ram erythrocytes in young Sprague-Dawley rats treated with cyclophosphamide (CTX)

| Treatment | Days from immunization | | | |
|---|---|---|---|---|
| | 12 | 20 | 29 | 40 |
| Non-immunized CTRL | 0 | 0 | 0 | 0 |
| Immunized CTRL | 32 | 128 | 512 | 1024 |
| Immun. + CTX | 0 | 4 | 16 | 16 |
| PSC 600 + CTX | 2 | 4 | 20 | 20 |

TABLE 12

Effect of PSC i.p. treatment on immunization with ram erythrocytes in old Sprague-Dawley rats treated with cyclophosphamide (CTX)

| Treatment | Days from immunization | | | |
|---|---|---|---|---|
| | 12 | 20 | 29 | 40 |
| Non-immunized CTRL | 0 | 0 | 0 | 0 |
| Immunized CTRL | 16 | 64 | 128 | 512 |
| Immun. + CTX | 0 | 0 | 16 | 16 |
| PSC 600 + CTX | 2 | 8 | 32 | 64 |

RESULTS

In young animals, treatment with CTX causes antibodies content suppression. PCS by intraperitoneal administration causes a considerable increase in antibodies levels both in young (Table 11) and old (Table 12) rats.

Tests in vitro

Blastization tests with concavaline A on splenocytes of young and old rats

Once the treatment with PSC previously described in the paragraph "Animals" was completed, the animals were sacrificed by decapitation, spleens were excised under sterile conditions and broken up in a Petri dish. The splenocytes thus obtained by mechanical dispersion were placed in culture medium RPMI 1640 with addition of calf fetal serum (FBS) (10%).

The resulting cellular suspension was centrifuged at 2500 rpm for 20 min on Ficoll-Paque gradient. Stratified splenocytes were taken by a sterile Pasteur pipette and washed three times with sterile FBS. Cells were counted and placed onto 96-well plastic plates at a concentration of $1\times10^5$/well in of volume of 0.1 ml. The cultures thus obtained were incubated for 48 hrs at 37° C., in a 5 carbon dioxide environment. Forty-eight hours later, concavaline A (ConcA) was added to the cultures at a concentration of 1 µg/ml in a volume of 0.1 ml. Eighteen hours later, tritiated thymidine was added (volume: 10 µl). Incorporation of tritiated thymidine was stopped after 3 hrs, by elimination of excess liquid by suction and by sucking the cells on fibreglass filters. Filters were placed in scintillation vials containing 5 ml of scintillating solution (Insta-Gel). Radioactivity (dpm) was measured during 2 min using a β-counter.

The results obtained on groups treated with ConA alone (controls), on groups treated with PSC (600 mg/kg), and on groups that had not been treated either with ConA or PSC are compared in Table 13.

TABLE 13

Effect of PSC i.p. treatment on blastization with concavaline A (ConA) of splenocytes of young and old Sprague-Dawley rats.

| Treatment | DPM × 100 | |
|---|---|---|
| | Young | Old |
| Controls | 1549 ± 69 | 1030 ± 24 |
| PSC 600 + ConA | 1488 ± 62 | 1250 ± 11* |
| non-ConA | 32 ± 2 | 35 ± 7 |

Results are expressed as the average value ± standard error.
*$P < 0.05$ (ANOVA followed by Duncan's test).

RESULTS

The animals treated with PSC (600 mg/kg) showed a significant increase in splenocytes blastization induced by ConA. Old animals showed a similar increase in the response to the mytogen in respect of controls, although the absolute values were significantly lower than those measured in young rats.

Response of circulating lymphoctyes to mytogens in young adult and old rats

Once the treatment with PSC previously described in the paragraph "Animals" was completed, the animals, both young and old, were sacrificed by decapitation and the blood collected in heparin-treated tubes. The blood samples were stratified on Ficoll-Paque gradient and centrifuged at 2500 rpm for 15 min. The lymphocytic cellular fraction was taken by suction and washed three times with a Lphysiological solution (0.9% NaCl). At the end of the treatment, the cells were resuspended in culture medium RPMI 1640 containing 10% FBS, counted ($1\times10^5$ cells/0.1 ml/well) and incubated for 48 hrs at 37° C., in a 5% carbon dioxide environment. At the incubation end, mitogens concavaline A (ConA) and phytohaemagglutinin (PHA) were added to the cultures at a concentration of 1 μg/ml in a volume of 0.1 ml. Eighteen hours later, tritiated thymidine (0.01 ml) was added to the cultures, subsequently incubated for 3 hrs. At the incubation end, cells were sucked by cell harvester and the filters were placed in scintillation vials with addition of 5 ml of scintillating solution. Radioactivity (dpm) was measured 2 min. using a β-counter.

The results obtained on ConA- or PHA-treated groups (controls), on PSC-treated groups (600 mg/kg), and on groups that had not been treated either with ConA or PSC are compared in Tables 14 and 15.

TABLE 14

Effect of PSC i.p. treatment on blastization with concavaline A (ConA) of peripheral lymphocytes of young and old Sprague-Dawley rats.

| Treatment | DPM × 100 | |
|---|---|---|
| | Young | Elderly |
| Controls | 671 ± 38 | 448 ± 39 |
| PSC 600 + ConA | 714 ± 23 | 512 ± 27* |
| non-ConA | 32 ± 3 | 28 ± 4 |

Results are expressed as the average value ± standard error.
*$P < 0.05$ (ANOVA followed by Duncan's test).

TABLE 15

Effect of PSC i.p. treatment on blastization with phytohaemagglutinin (PHA) of peripheral lymphocytes of young and old Sprague-Dawley rats.

| Treatment | DPM × 100 | |
|---|---|---|
| | Young | Elderly |
| Controls | 749 ± 26 | 385 ± 27 |
| PSC 600 + PHA | 703 ± 44 | 533 ± 29* |
| non-PHA | 30 ± 5 | 32 ± 5 |

Results are expressed as the average value ± standard error.
*$P < 0.05$ (ANOVA followed by Duncan's test).

RESULTS

In peripheral lymphocytes, the incorporation index of tritiated thymidine in young rats did not differ from controls. Old rats treated with PSC (600 mg/kg) showed an increased index of thymidine incorporation in respect of controls.

The results obtained are analogous for the two mitogens used (ConA and PHA) (Tables 14 and 15).

Interleukin-2 (IL-2) production following interleukin-1(IL-1) i.p. injection in young and old rats With a view to evaluating a further aspect of the immunological activity in PSC-treated (600 mg/kg) animals, according to the aforementioned scheme, an investigation was carried out on interleukin-2 (IL-2) response to the injection of IL-1 that, as known, stimulates IL-2 production from lymphocytes.

Once the treatment was completed, each rat was administered IL-1 (0.1 mg/kg, i.p.). One hour after injection, the animals were killed by decapitation, the blood was collected and centrifuged, and the plasma maintained at −20° C. until IL-2 dosing.

The evaluation of IL-2 production was based on an immunological assay, utilizing a specific antibody produced in heterologous species against rat IL-2. Samples were assayed twice.

The results obtained are shown in Table 16. The controls are rats treated only with IL-1.

TABLE 16

| Stimulation | Controls | PSC 600 mg/Kg |
|---|---|---|
| Saline, young | n.d. | n.d. |
| IL-1, young | 305 ± 19 | 284 ± 20 |
| Saline, old | n.d. | n.d. |
| IL-1, old | 117 ± 9 | 219 ± 6* |

RESULTS

IL-2 levels could not be determined in rats injected with saline solution (0.9% NaCl). IL-2 levels in old rats are lower than in the young ones, although significant increases were detected in the groups treated i.p. with PSC (Table 16).

TUMOUR PROLIFERATION
1. TRANSPLANTABLE NEOPLASMS

Animals

Male adult BALB/c mice weighing 20 g were stabled under standard conditions (24°±1° C., 12 h light/dark cycle, free access to food and water). Handlings were made in such a way as to avoid stressful stimuli.

Pharmacological treatment

All animals, subdivided into groups of 6, were treated 4 weeks with a PSC dose (600 mg/kg). After a 2 week treatment, the mice were inoculated intramuscularly (i.m.) with murine fibrosarcoma WEHI 164 clone 13 cells or Lewis lung carcinoma in an amount of $1\times10^5$ cells. Treatment was continued two weeks after tumour inoculation. The mice were sacrificed and the tumoral mass growth and the development of metastases, if any, were evaluated. The results obtained are shown in Tables 17 and 18.

TABLE 17

Effect of 30 days' PSC treatment (600 mg/kg, i.p.) on tumoural mass growth in BALB/c mice, 7 and 15 days after inoculation of murine fibrosarcoma cells (WEHI 164 clone 13)

| Treatment | Tumoral mass diameter (cm) | |
|---|---|---|
| | 7th day | 15th day |
| Non-treated CTRL | 0.8 ± 0.01 | 2.5 ± 0.1 |
| PSC 600 mg/kg | n.d. | 0.6 ± 0.03 |

Results are expressed as the average value ± standard error.
*P < 0.05 (ANOVA followed by Duncan's test).

TABLE 18

Effect of 30 days' PSC treatment (600 mg/kg, i.p.) on metastases development in BALB/c mice, 15 days after inoculation of Lewis lung carcinoma cells

| Treatment | Mice with metastases/group | % |
|---|---|---|
| Non-treated CTRL | 6/6 | 100 |
| PSC 600 mg/kg | 2/6 | 33 |

RESULTS

The use of PSC (600 mg/kg) in neoplastic experimental models on BALB/c mice prevented tumoural growth, as proved by a decreased tumoural mass growth in animals inoculated with murine fibrosarcoma cells (WEHI 164 clone 13) (Table 17), and slows down the metastatic process in animals inoculated with Lewis lung carcinoma cells (Table 18).

2. URETHANE-INDUCED TUMOURS OF THE LUNGS

Male albino adult Swiss mice (20–25 g) were used. All animals were inoculated i.p. with urethane. The animals were treated with PSC (600 mg/kg) 15 days prior to and after inoculation. Once the treatment was completed, the animals were sacrificed, their lungs excised and subjected to necro-histologic examination. The results obtained are shown in Table 19.

TABLE 19

Effect of 30 days' PSC treatment (600 mg/kg, i.p.) on the development of tumours of the lungs in albino Swiss mice, 15 days after i.p. injection of urethane

| Treatment | Mice with neoplasms/group | % |
|---|---|---|
| Non-treated with PSC | 6/6 | 100 |
| PSC 600 mg/kg | 3/6 | 50 |

RESULTS

PSC chronic treatment in albino Swiss mice significantly slowed down the development of tumours of the lungs induced by i.p. administration of cancerogenic urethane (Table 19).

CONCLUSIONS

The data obtained from the immunological tests provide evidence for a significant immunestimulating action of PSC.

In fact, PSC exerts an immunostimulating action on classical immunological parameters, such as proliferation due to mitegens on splenocytes and peripheral lymphocytes, and is also effective in restoring a correct immunological functionality in CTX-immunodepressed old rat.

Furthermore, a marked effect of PSC was observed as concerns IL-2 production after stimulation with IL-1. In fact, after treatment with PSC, the IL-2 plasma levels that may be measured by the RIA method in old rats were similar to those observed in young rats.

PSC is also notably active in hindering tumoural growth; in particular it significantly slows down the growth of fibrosarcomatous tumours in the rat as well as the metastatic spreading of other tumoural lines.

An important datum emerging from the examination of the antineoplastic effect of PSC is that its action seems most potent on the tumours directly induced by contact with a chemical carcinogen, such as urethane. This is a further proof that PSC especially acts as an antagonist of compounds with a given electric charge, not only in general medicine, but also in oncology.

Said preventive action on chemicals-induced tumours is highly important as it may be correlated with the prevention of tumours in highly carcinogens-polluted environments.

Furthermore, treatment with PSC did not significantly affect the behaviour and death rate of the various test groups. In particular, no death occurred in all tested groups.

PHARMACOLOGICAL TESTS ON INFERTILITY

EFFECT OF PSC ON THE SPERMATIC PRODUCTION OF FREE RADICALS

A direct analysis of free radicals production from spermatozoa was carried out with luminol (LM), a substance used in chemiluminescence, capable of permeating spermatozoa, thus revealing the free radicals intracellular presence.

Free radicals production was investigated under basal and maximal conditions (after A23187 addition) on controls and in the presence of PSC.

A23187 is an ionophore bivalent cation that, under physiological conditions, promotes acrosomial reaction. It is used being capable of stimulating the production of superoxide radicals (Aitken R. J. et al., Generation of reactive oxygen species, lipid peroxidation and human sperm function, J. of Reproduction, 40, 183–197, 1989).

Seminal fluid was obtained from 11 donors previously subjected to a complete medical check-up, to exclude the presence, if any, of sexual transmission diseases. Samples were obtained by masturbation and analysed within 1.5 hrs thereafter.

Spermatozoa were separated from seminal fluid by three centrifugation cycles (500×g for 5 min) and resuspended in medium BWW (Biggers et al., "The culture of mouse embryos in vitro", Daniel J. C. ed., Methods in mammalian embryology, 86–116, 1971) at a concentration of $20\times10^6$/ml.

The production of reactive oxygen species (ROS) was evaluated by chemiluminescence with luminol: human spermatozoa suspensions at a concentration of $20\times10^6$ ml in a volume of 500 µl were subjected to the action of luminol (LM 100 mmol/l in dimethyl sulphoxide). Said spermatic suspension was then diluted with 500 µl of medium BWW alone (control) or containing PSC (10 mM); other spermatic suspensions contained A23187 (0.05 mg/ml) alone (positive control) and, respectively, A23187 (0.05 mg/ml)+PSC (10 mM).

3 Minutes later, the chemiluminescent signal was recorded. Reactive oxygen species (ROS) production was expressed as photons brust (cpm) recorded by a luminometer Berthold L 9500.

The results shown in Table 20 provide evidence that PSC caused a significant reduction in free radicals production, both under basal and maximal conditions.

TABLE 20

| ROS production, expressed as photons brust (cpm) recorded by luminometer, in the presence and in the absence of PSC | |
|---|---|
| Spermatic suspension | ROS |
| medium alone | 607.7 +/− 160.3 |
| medium + PSC | 243.7 +/− 235.2 |
| medium + A23187 | 3530.1 +/− 849.8 |
| medium + A23187 + PSC | 270.8 +/− 254 |

PHARMACOLOGICAL TESTS ON SNC

PSC EFFECT ON LIPID PEROXIDATION IN RAT SNC

Since lipid peroxidation, i.e. the oxidation of an α-methylenic bridge of a polyunsaturated fatty acid, is a process that, through the formation of intermediates (such as lipid peroxides and hydroperoxides), provide carbonyl fragments, including malonic aldehyde (MDA), efforts were made by the Applicant to check whether administration of the test molecule might reduce MDA levels in the SNC, which are closely related to the presence of free radicals and, consequently, to a potential neuronal damage, which is strongly responsible for the induction of age-related alterations.

The test was carried out on male Wistar rats stabled in groups of 5/cage, at 21° C. and constant light/dark cycle, fed with standard laboratory food.

Malonic anhydride was assayed both on young and old rats, prior to and after treatment with PSC (100 mg/kg). A few hours after treatment, all animals were sacrificed and their brain readily excised. MDA was determined by a micromethod modified according to Slater and Sawyer (Slater T. F. and Sawyer B. C., 1971, J. Biochem., Tokio 8: 2180). The tissue was maintained 10 min. at 0° C. in 0.05M Tris-HCl buffer, pH 7.4, and homogenized. A portion of brain homogenate (0.5 ml) was extracted with trichloroacetic acid (TCA) (20%, p/v). After centrifuging, 0.9 ml of the supernatant was added to 1 ml of 0.67% thiobarbituric acid in 0.026M of Tris-HCl buffer, pH 7.0. Samples were placed in boiling water for 10 min. After cooling, the absorbance at 532 nm was recorded by a spectrophotometer. MDA was expressed in nmoles/mg proteins. Proteins were measured by Smith's method using, as a reagent, bicinchoninic acid (BCA) (Smith et al., 1985, Anal. Biochem., 27, 502). The results obtained are recapitulated in Table 21.

TABLE 21

| MDA production in young animals, in control old animals, and in old animals after i.p. administration of PSC (100 mg/kg) | |
|---|---|
| Group of animals | MDA (nmols/mg proteins) |
| young animals | 0.573 +/− 0.19 |
| control old animals | 1.18 +/− 0.13 |

TABLE 21-continued

| MDA production in young animals, in control old animals, and in old animals after i.p. administration of PSC (100 mg/kg) | |
|---|---|
| Group of animals | MDA (nmols/mg proteins) |
| PSC-treated old animals | 0.723 +/− 0.32 |

I claim:

1. An acyl derivative of L-pyroglutamyl-L-cysteine of formula (I)

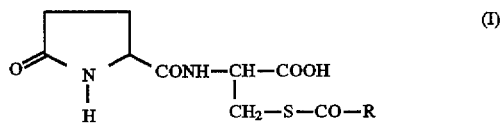

where R is a linear or branched alkyl group containing from 1 to 6 carbon atoms, or their pharmaceutically acceptable salts.

2. The derivative of formula (I) according to claim 1, wherein R is $CH_3$.

3. A process for the preparation of an acyl derivative of L-pyroglutamyl-L-cysteine of formula (I)

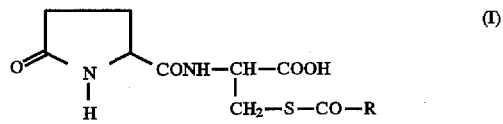

where R is a linear or branched chain alkyl containing 1 to 6 carbon atoms, comprising the following steps:

a) treating L-2-pyrrolidone-5-carboxylic acid with a compound R'OH, where R' is a phenyl substituted with one or more substituents selected from the group consisting of halogens and nitro-groups, in the presence of dicyclohexyl carbodiimide as coupling agent, in an organic polar solvent, to give an ester of formula (II)

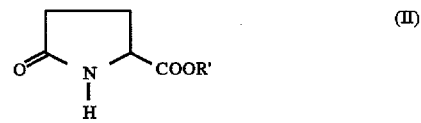

where R' is as defined above, b) treating the ester of formula (II) with an L-cysteine of formula (III)

where R" is a sulphur protective group of the —SH function selected from the group consisting of benzyl and $NH_2$—$CH(COOH)CH_2S$—, to give an amide derivative of L-pyroglutamic acid of formula (IV)

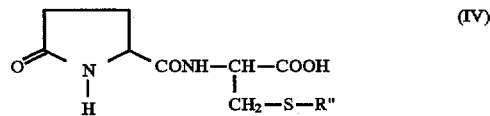

c) removing the sulphur protective group by treatment with a reducing system selected from the group consisting of Na in liquid $NH_3$ and $H_2$ in the presence of Pd on carbon as the catalyst to give L-pyroglutamyl-L-cysteine of formula (V)

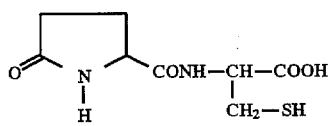 (V)

d) acylating L-pyroglutamyl-L-cysteine by treatment with an acylating agent selected from the group consisting of carboxylic acid anhydrides, mixed anhydrides derived from carboxylic acids and halocarbonates, and acyl halides in the presence of a catalyst selected from the group consisting of acids and bases, in a polar solvent, provided that pyridine is not used as the reaction solvent to give the acyl derivative of formula (I).

4. The process according to claim 3, wherein compound R'OH is selected from the group consisting of pentachlorophenol, p-nitrophenol, and 2,4-dinitrophenol, the operating temperature of step a) ranges between −10° C. and +10° C., steps a) and b) are carried out using a polar solvent selected from the group consisting of dimethylsulphoxide, dimethylformamide and dioxane the temperature of step b) is room temperature, the catalyst of step d) is selected from the group consisting of sulphuric acid, sodium bicarbonate, and triethylamine, and the temperature of step d) ranges between −10° and +10° C.

5. The process according to claim 4 wherein R'OH is pentachlorophenol, group R" is benzyl, step b) is carried out in the presence of triethylamine, step c) is carried out with liquid ammonia, the acylating agent is a carboxylic acid anhydride, and the catalyst of step d) is sodium bicarbonate, the temperature in steps a) and d) is between 0° and +5° C.

6. The process according to claim 5 wherein the anhydride is acetic anhydride which is used as the reaction medium.

7. Process for the preparation of an acyl derivatives of L-pyroglutamyl-L-cysteine of formula (I),

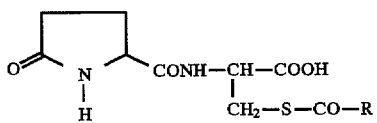 (I)

wherein R is a linear or branched alkyl group containing from 1 to 6 carbon atoms, comprising the following steps:

a') treating L-2-pyrrolidon-5-carboxylic acid with an L-cysteine ester of formula (VI):

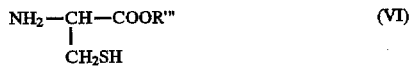 (VI)

wherein R'" is the residue of a protecting group of a carboxylic function selected from the group consisting of i) linear or branched alkyl groups of from 1 to 6 carbon atoms, ii) 3–10 membered alicyclic groups, iii) 6–10 membered aromatic groups, iv) a group selected from the group consisting of i), ii) and iii) substituted with from 1 to 3 groups selected from the group consisting of linear or branched alkyl groups of from 1 to 6 carbon atoms, linear or branched alkoxy radicals of from 1 to 6 carbon atoms, halogen atoms and 6–10 membered aromatic residues; and v) a member selected from the group consisting of i) and ii) substituted with at least one ethylenic or acetylenic unsaturation, in an inert organic solvent, in the presence of dicyclohexyl carbodiimide as a coupling agent;

b') hydrolyzing the ester group contained in the L-pyrroglutamyl-L-cysteine ester of formula (VII)

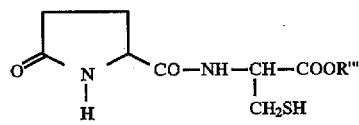 (VII)

obtained in the preceding step, wherein R'" has the above mentioned meaning, by reacting this compound with an organic or inorganic base in the presence of water, and subsequently acidifying the reaction mixture: c') reacting L-pyroglutamyl-L-cysteine, coming from the preceding step, with an acylating agent selected from the group consisting of carboxylic acid anhydrides, mixed anhydrides obtained from carboxylic acids and halocarbonates, and acyl halides, in the presence of an acid or basic catalyst, in a polar solvent provided that pyridine is not used as the reaction solvent.

8. Process as claimed in claimed 7, wherein R'" is CH$_3$.

9. Process as claimed in claim 7, wherein in step a') the inert organic solvent is selected from the group consisting of dimethylsulfoxide, dimethylformamide, dioxane, ethyl acetate, chloroform, methylene chloride and any mixture thereof; the temperature in step a') is comprised between −40°C. and +70° C.: step b') is carried out in water alone, or in water in admixture with a cosolvent selected from the group consisting of dioxane, dimethylformamide and an alcohol using a base selected from the group consisting of hydroxides, carbonates and bicarbonates of alkali-metals, alkali-earth metals and ammonium; tertiary aliphatic and aromatic amines; and heterocyclic aromatic bases; the temperature of step b') is comprised between +20° and +70° C.; instep c') the catalyst is selected from the group consisting of sulphuric acid, sodium bicarbonate and triethylamine and the temperature is comprised between −10° and +10° C.

10. Process as claimed in claim 9, wherein in step a') the derivative of formula (VI) is used in the form of a salt with an acid, and step a') is carried out in the presence of a base selected from the group consisting of tertiary aliphatic amines, tertiary aromatic amines and heterocyclic bases, at a temperature comprised between −10° and +10° C., and the solvent is dimethylformamide; the temperature in step c') is between 0° and +5° C.; the acylating agent is an anhydride of a carboxylic acid; the catalyst of step c') is sodium bicarbonate.

11. Therapeutic compositions containing, as active ingredient, an effective dose of at least one of L-pyroglutmayl-L-cystiene acyl derivative of formula (I)

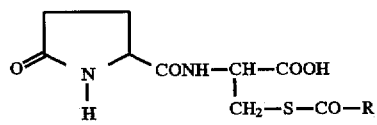 (I)

where R is a linear of branched alkyl; having 1 to 6 carbon atoms or of a pharmaceutically acceptable salt therof, in combination with suitable excipients.

12. The therapeutic compositions according to claim 11 that are suitable for oral administration.

13. The therapeutic compositions according to claim 11 that are suitable for parenteral administration.

14. The therapeutic compositions according to claim 12 wherein the active ingredient amount ranges between 100 and 3000 mg.

15. The therapeutic compositions according to claim 13 wherein the active ingredient amount ranges between 30 and 2000 mg.

16. A therapeutic method for the treatment of disease connected with glutathione deficiency in a patient, comprising administering to said patient an effective amount of at least one derivative of formula (I):

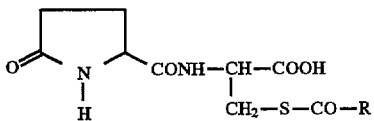

wherein R is a linear or branched chain alkyl group containing from 1 to 6 carbon atoms, or a pharmaceutically acceptable salt thereof.

17. The method as claimed in claim 16, wherein said effective amount is orally or parenterally administered.

18. The method as claimed in claim 17, wherein the effective amount which is orally administered ranges from 5 to 50 mg/kg/die.

19. The method as claimed in claim 17, wherein the effective amount which is parenterally administered ranges from 1 to 30 mg/kg/die.

20. A process as claimed in claim 7, wherein the acylating agent is acetic anhydride which is used as the reaction medium.

21. A method as claimed in claim 16, wherein the disease is a hepatic disease.

22. A method as claimed in claim 16, wherein the disease is a disorder following acute or chronic alcohol abuse.

23. The method as claimed in claim 16, wherein the disease is intoxication from a drug or chemical agent.

24. The method as claimed in claim 16, wherein the drug in a chemotherapeutic, antineoplastic or antitubercular drug.

25. The method as claimed in claim 16, for the treatment of disorders due to exposure to xenobiotic agents in a patient.

26. The method as claimed in claim 16, for the prophylaxis or treatment of damages caused by radiation.

27. The method as claimed in claim 16, for the treatment of poisoning from heavy metals.

28. A therapeutic method for the treatment of disorders associated with physiological brain aging or of acute or chronic neurodegenerative diseases in a patient, comprising administering to said patient an effective amount of at least one derivative of formula (I)

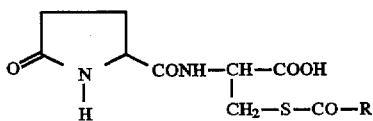

wherein R is a linear or branched alkyl group containing from 1 to 6 carbon atoms, or of a pharmaceutically acceptable salt thereof.

29. The method as claimed in claim 28, wherein the disorders associated with physiological brain aging are selected from the group consisting of Parkinson's disease, brain degeneration due to decreased glutathione levels, loss of memory and loss of capability of learning.

30. The therapeutic method of claim 28, wherein chronic neurodegenerative diseases are selected from the group consisting of amyotrophic lateral sclerosis, Alzheimer's disease and Huntington's chorea.

31. A therapeutic method for the treatment of diseases related to an altered functionality of the immune system in a patient, comprising administering to said patient an effective amount of at least one derivative of formula (I)

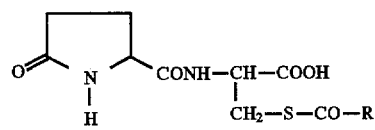

wherein R is a linear or branched alkyl group containing from 1 to 6 carbon atoms, or a pharmaceutically acceptable salt thereof.

32. A therapeutic method for the treatment of a tumor which is a chemically induced tumor in a patient, said method comprising administering to said patients an effective amount of at least one derivative of formula (I):

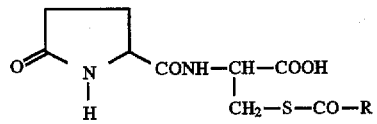

wherein R is a linear or branched alkyl group containing from 1 to 6 carbon atoms, or a pharmaceutically acceptable salt thereof.

33. A therapeutic method for the treatment of a tumor selected from the group consisting of fibrosarcomatous tumors and lung tumors in a patient, said method comprising administering to said patient an effective amount of at least one derivative of formula (I):

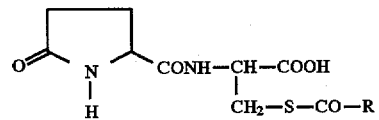

wherein R is a linear or branched alkyl group containing from 1 to 6 carbon atoms, or a pharmaceutically acceptable salt thereof.

34. A therapeutic method for the treatment of a metastatic tumor in a patient, said method comprising administering to said patient an effective amount of at least one derivative of formula (I):

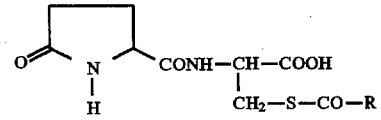

wherein R is a linear or branched alkyl group containing from 1 to 6 carbon atoms, or a pharmaceutically acceptable salt thereof.

35. A therapeutic method for the treatment of infertility in a male patient, comprising administering to said male patient an effective amount of at least one derivative of formula (I)

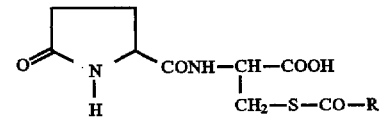

wherein R is a linear or branched alkyl group containing from 1 to 6 carbon atoms, or a pharmaceutically acceptable salt thereof.

36. The therapeutic method as claimed in claim 28, wherein acute neurodegenerative disease are selected from the group consisting of acute ischaemic states, cerebral ictus, hypoglycaemia, or epileptic attacks.

37. A therapeutic method for the treatment of urethane induced tumors of the lung in a patient, said method comprising administering to said patient an effective amount of at least one derivative of formula (I):
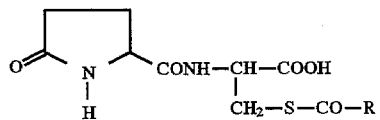
wherein R is a linear or branched alkyl group containing from 1 to 6 carbon atoms, or a pharmaceutically salt thereof.
* * * * *